US011406758B2

(12) United States Patent
List

(10) Patent No.: US 11,406,758 B2
(45) Date of Patent: Aug. 9, 2022

(54) CONNECTOR DEVICE

(71) Applicant: Roche Diabetes Care, Inc., Indianapolis, IN (US)

(72) Inventor: Hans List, Oberzent (DE)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 108 days.

(21) Appl. No.: 16/326,577

(22) PCT Filed: Aug. 18, 2017

(86) PCT No.: PCT/EP2017/070906
§ 371 (c)(1),
(2) Date: Feb. 19, 2019

(87) PCT Pub. No.: WO2018/041645
PCT Pub. Date: Mar. 8, 2018

(65) Prior Publication Data
US 2019/0240401 A1 Aug. 8, 2019

(30) Foreign Application Priority Data
Aug. 29, 2016 (EP) .................................... 16186167

(51) Int. Cl.
*A61M 5/168* (2006.01)
*A61M 39/26* (2006.01)
(Continued)

(52) U.S. Cl.
CPC .... *A61M 5/16813* (2013.01); *A61M 5/14248* (2013.01); *A61M 5/158* (2013.01);
(Continued)

(58) Field of Classification Search
CPC .. A61M 5/16813; A61M 39/26; A61M 39/22; A61M 5/14248; A61M 2039/0226;
(Continued)

(56) References Cited

U.S. PATENT DOCUMENTS 6,089,541 A * 7/2000 Weinheimer .......... A61M 39/26
251/149.1
7,891,637 B2 2/2011 Zimmermann et al.
(Continued)

FOREIGN PATENT DOCUMENTS

JP    S5618834 B2    5/1981
JP    2014040921 A   10/2013
(Continued)

OTHER PUBLICATIONS

International Patent Application PCT/EP2017/070906 International Preliminary Report on Patentability dated Nov. 27, 2018. 18 pages.
(Continued)

*Primary Examiner* — Amber R Stiles
*Assistant Examiner* — Avery Smale
(74) *Attorney, Agent, or Firm* — Woodard, Emhardt, Henry, Reeves & Wagner, LLP

(57) ABSTRACT

A first connector part (110) for establishing a fluid connection with a second connector part comprises a valve (111) with a valve seat (112), the valve seat comprising a valve chamber (116) and a circular opening with a circumferential sealing lip (114); a valve member (113), the valve member being provided in the valve chamber, and being able to sealingly close the circular opening of the valve seat when being pushed against the circular opening; and a resilient element (115) that subjects the valve member to a bias force pushing the valve member against the circular opening of the valve seat. The valve member further comprises a circumferential wall around the circular opening, located on a side of the circular opening opposite to the valve chamber. The circumferential wall forms a concave receptacle (118) for receiving a right circular truncated cone of the second connector part, the concave receptacle having a shape of a truncated cone and facing away from the valve chamber, the (Continued)

circular opening being located in a center of the concave receptacle. The second connector part (150) for establishing the fluid connection with the first connector part comprises the right circular truncated cone (151) for being received in the concave receptacle of the first connector part; a recess (153) at a tip of the right circular truncated cone for actuating the valve member of the first connector part; and a fluid feed conduit (152). The fluid feed conduit has one or more outlets (154) opening at least partially toward a shell surface of the right circular truncated cone (151).

27 Claims, 8 Drawing Sheets

(51) Int. Cl.
*A61M 39/10* (2006.01)
*A61M 39/22* (2006.01)
*A61M 5/142* (2006.01)
*A61M 5/158* (2006.01)
*A61M 39/02* (2006.01)

(52) U.S. Cl.
CPC ............ *A61M 39/10* (2013.01); *A61M 39/22* (2013.01); *A61M 39/26* (2013.01); *A61M 2005/14252* (2013.01); *A61M 2005/1585* (2013.01); *A61M 2039/0226* (2013.01); *A61M 2039/1072* (2013.01); *A61M 2039/1077* (2013.01); *A61M 2039/226* (2013.01)

(58) Field of Classification Search
CPC .. A61M 2039/1072; A61M 2039/1077; A61M 2039/248; A61M 5/158; A61M 39/10; A61M 2005/1585; A61M 2039/226; A61M 5/14244; A61M 2005/14272; A61M 2005/1586; A61M 2039/0205; A61M 2039/027; A61M 2039/0294; A61M 2039/1061; A61M 2039/2473
See application file for complete search history.

(56) References Cited

U.S. PATENT DOCUMENTS

| | | | |
|---|---|---|---|
| 8,430,847 B2 | 4/2013 | Mernoe et al. | |
| 2004/0148718 A1 | 8/2004 | Michel | |
| 2006/0289177 A1 | 12/2006 | Cuadrado | |
| 2008/0288144 A1 | 11/2008 | Jeppe et al. | |
| 2008/0303267 A1* | 12/2008 | Schnell | A61M 39/10 285/26 |
| 2009/0198215 A1 | 8/2009 | Chong et al. | |
| 2012/0211946 A1* | 8/2012 | Halili | A61M 5/31 277/607 |
| 2012/0296290 A1 | 11/2012 | Argauer et al. | |
| 2014/0378912 A1 | 12/2014 | Halili et al. | |
| 2015/0105731 A1* | 4/2015 | Montalvo | A61M 5/158 604/180 |

FOREIGN PATENT DOCUMENTS

| | | |
|---|---|---|
| WO | 2002007804 A1 | 1/2002 |
| WO | 2007056504 A1 | 5/2007 |
| WO | 2013153722 A1 | 10/2013 |

OTHER PUBLICATIONS

EP Application No. 16186167.9, Office Action dated Dec. 18, 2018.
JPO, JP App. No. JP2019-510422 Office Action with translation in part, 8 pages, dated Oct. 26, 2021.
JPO, JP App. No. JP2019-510422 Office Action with translation in part, 20 pages, dated May 25, 2021.

* cited by examiner

Fig. 1 --PRIOR ART--
Fig. 2
(e)
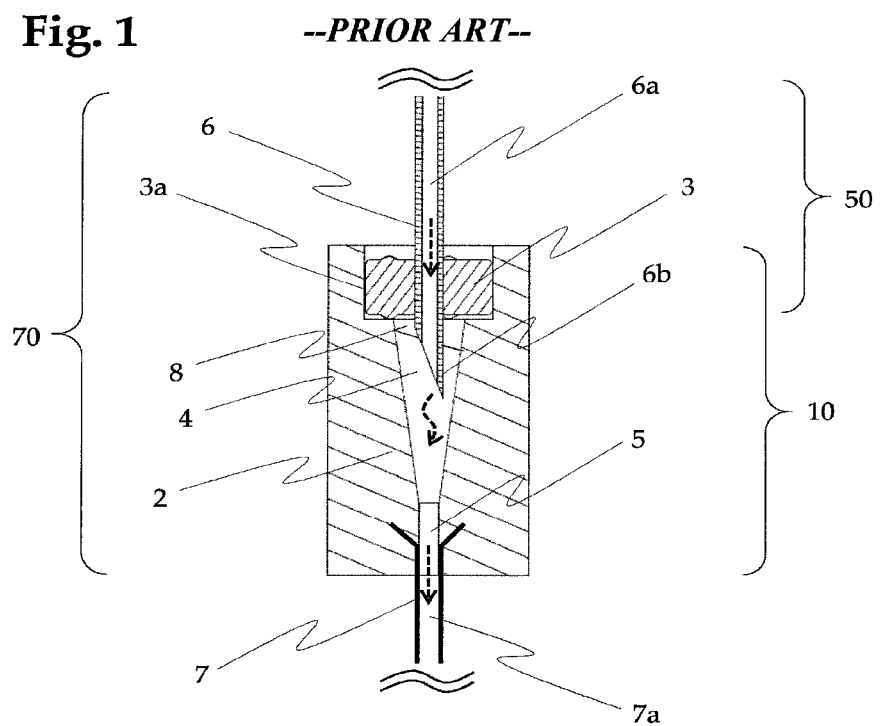
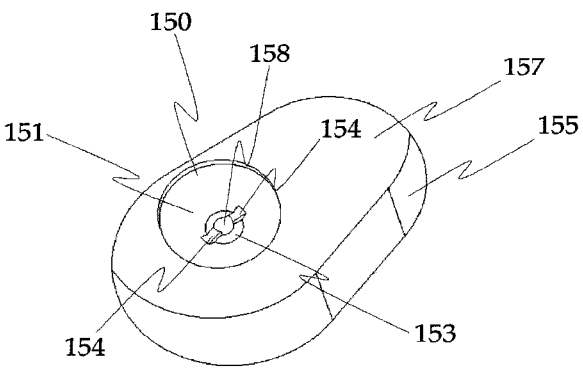

Fig. 2
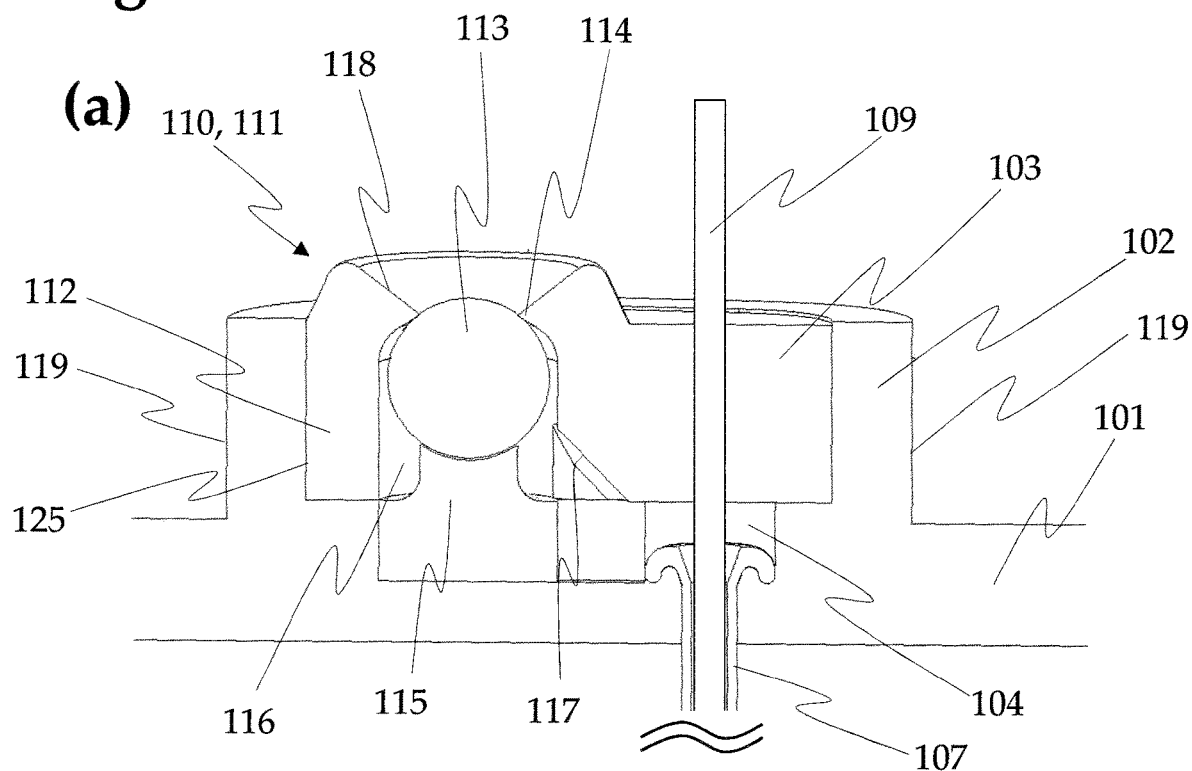
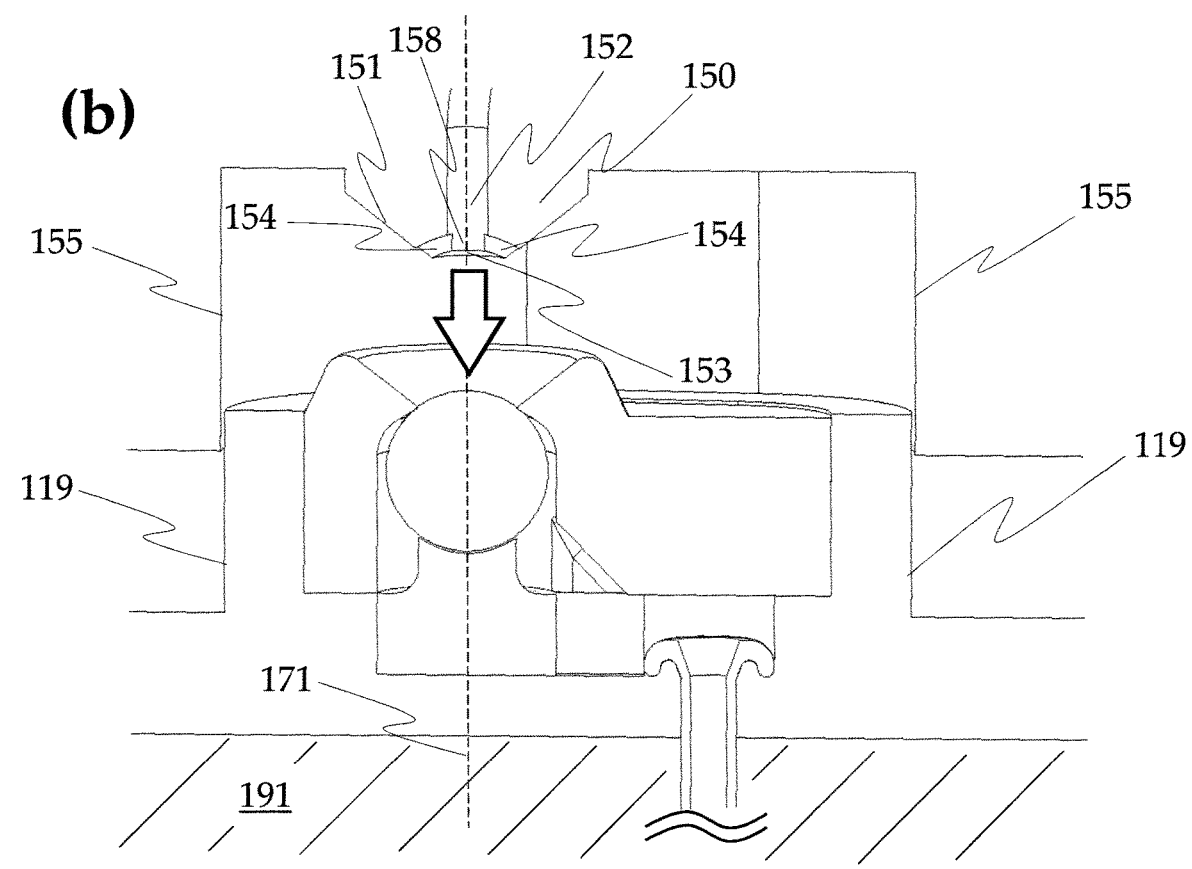

Fig. 2
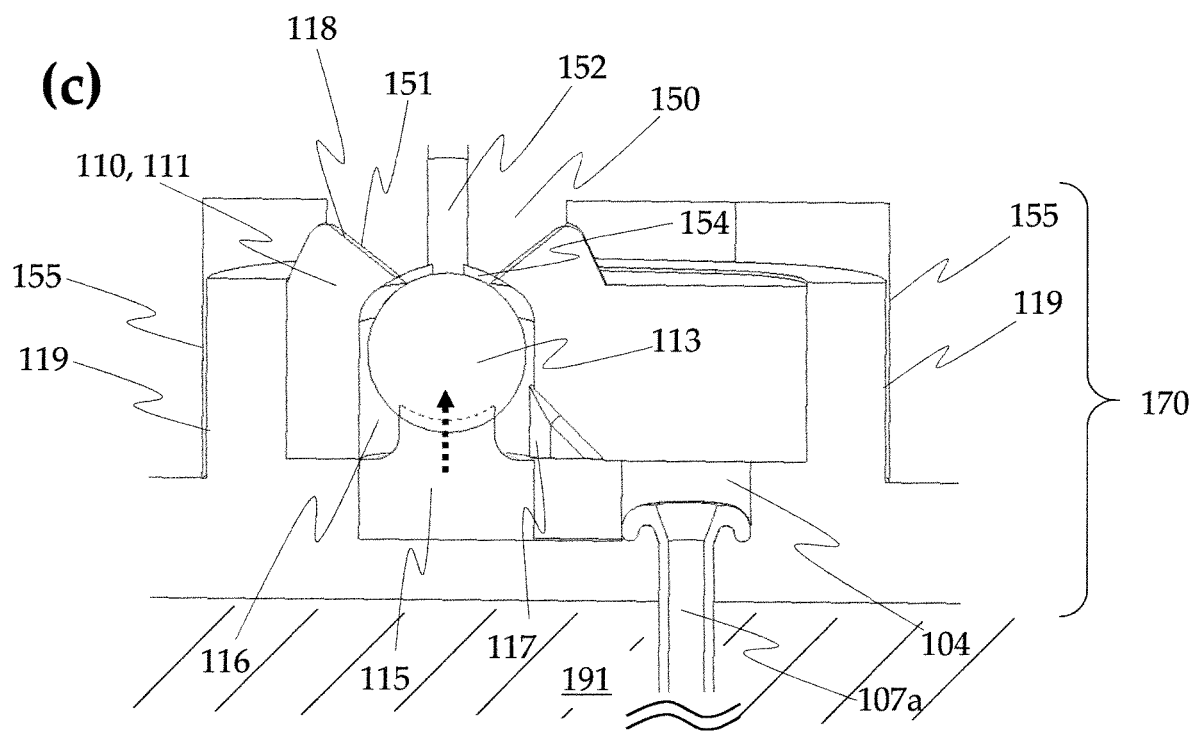
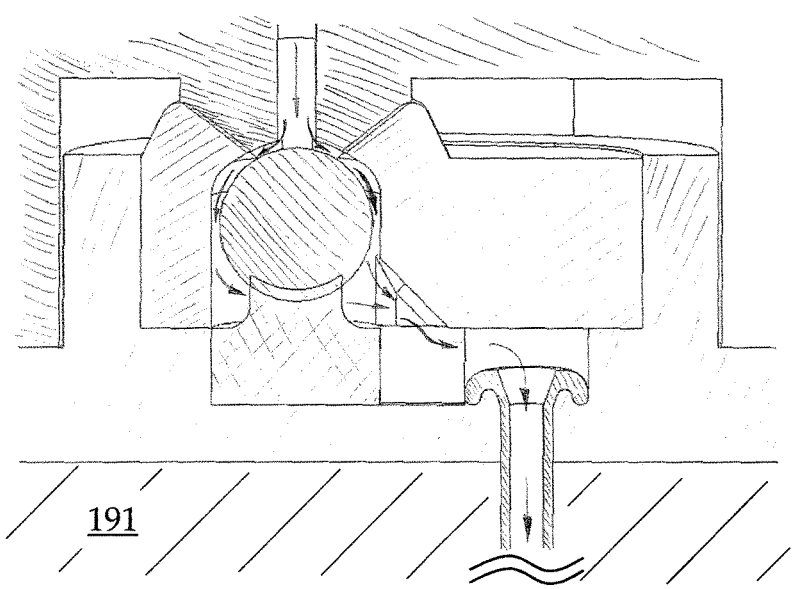

Fig. 3
(a)
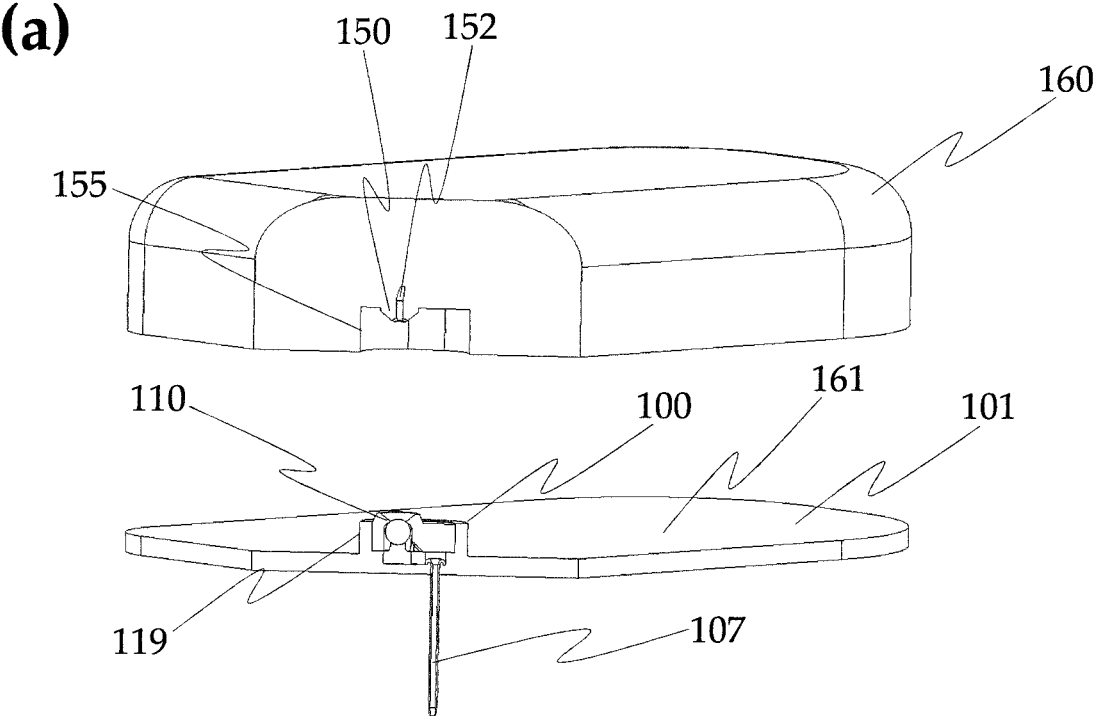
(b)
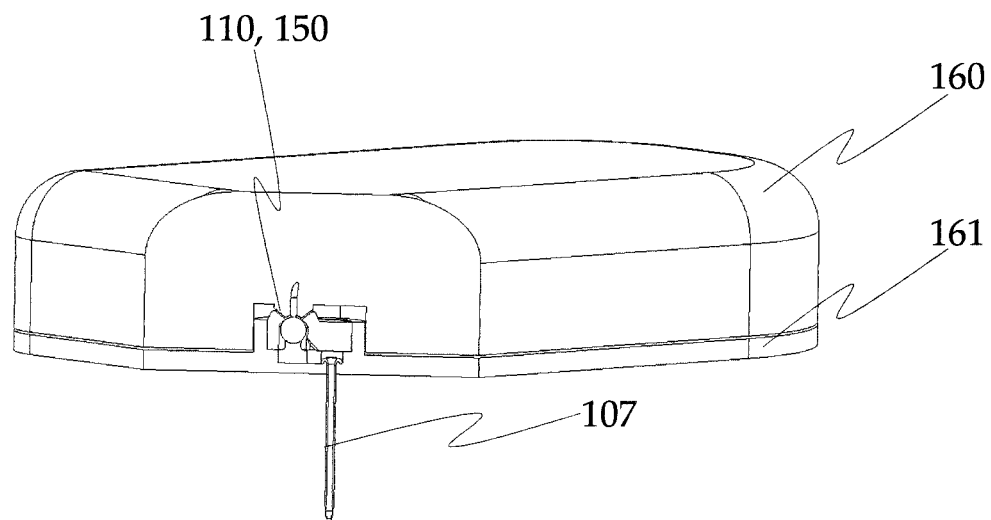

Fig. 4
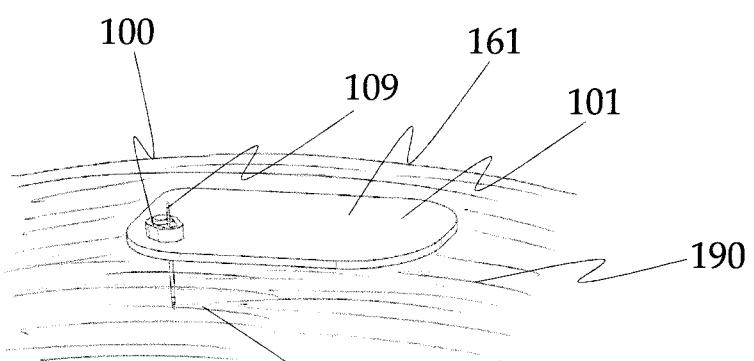
(a)
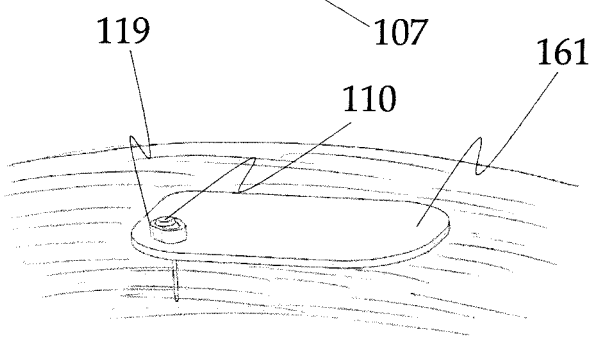
(b)
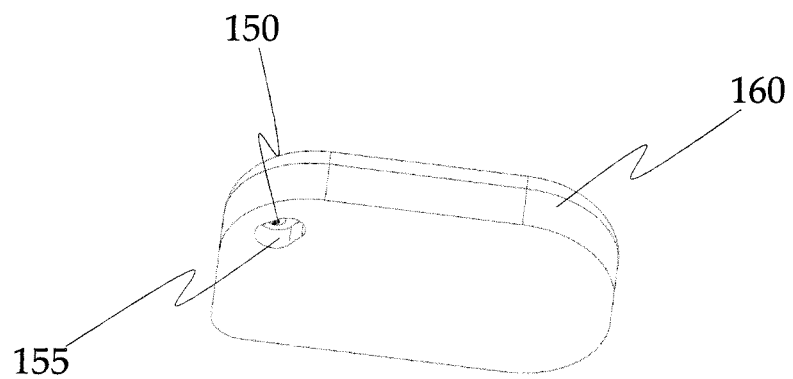
(c)
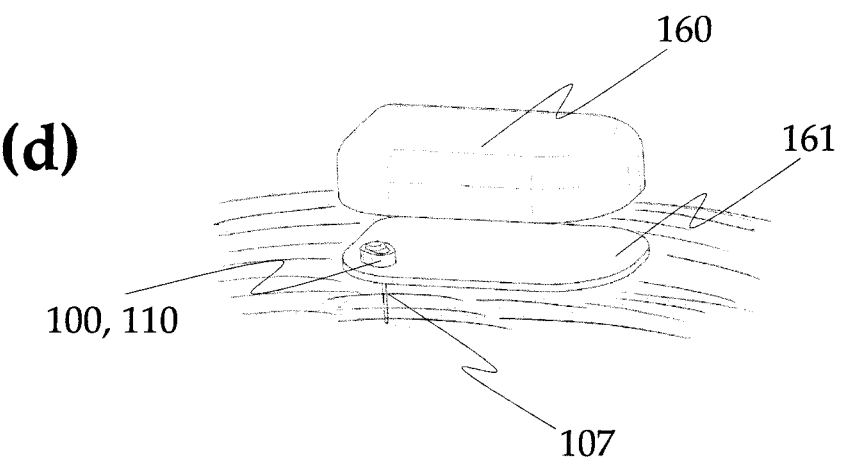
(d)

Fig. 5
(a) 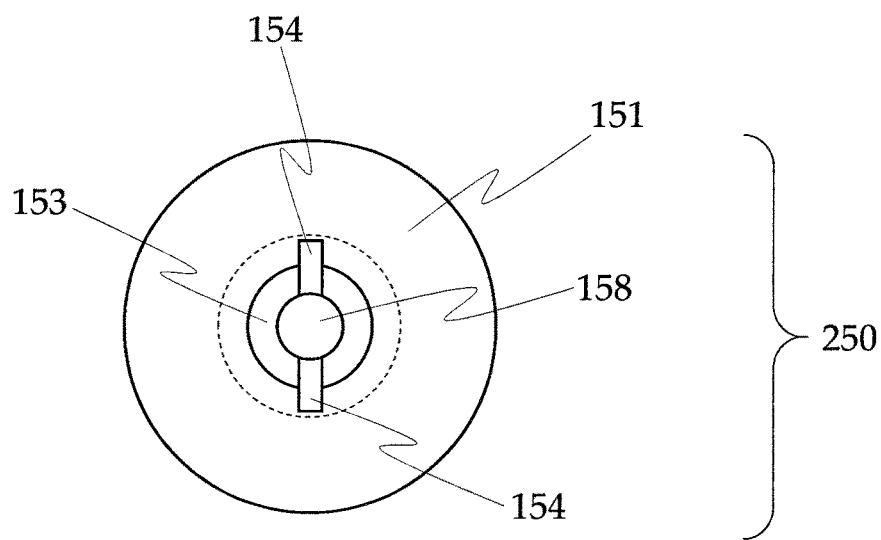
(b) 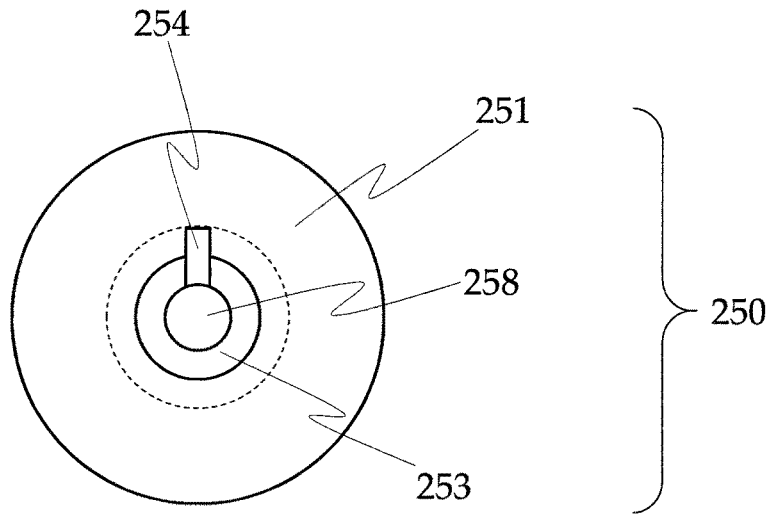
(c) 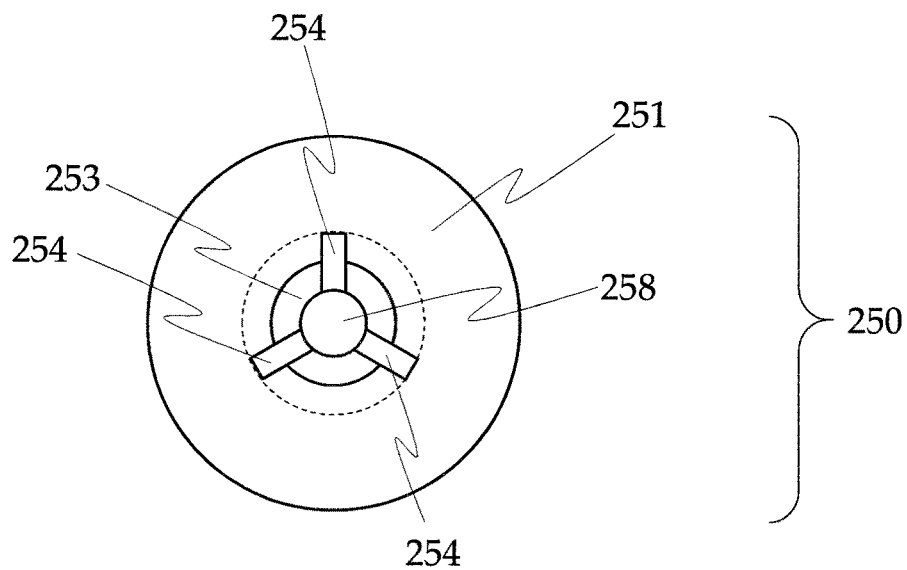

Fig. 5
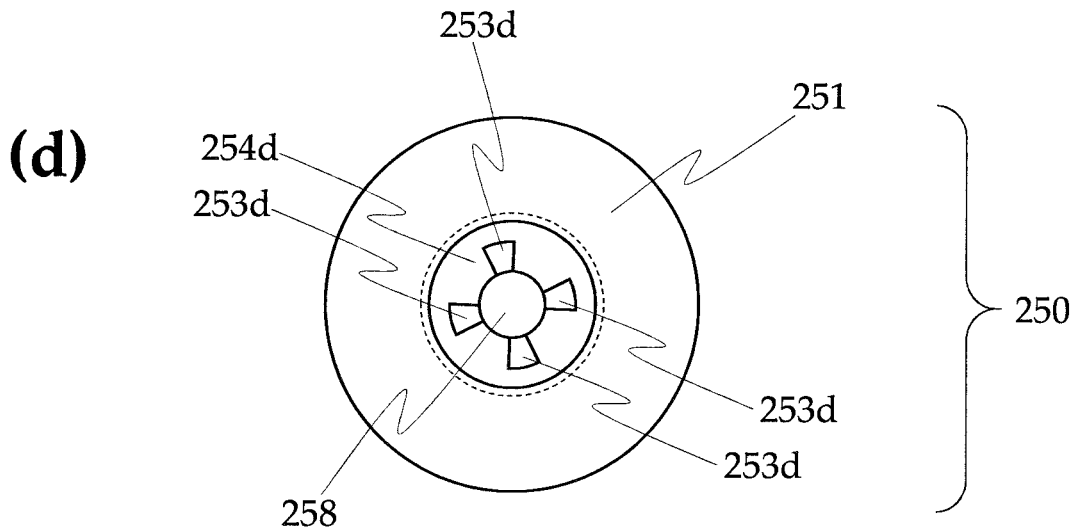
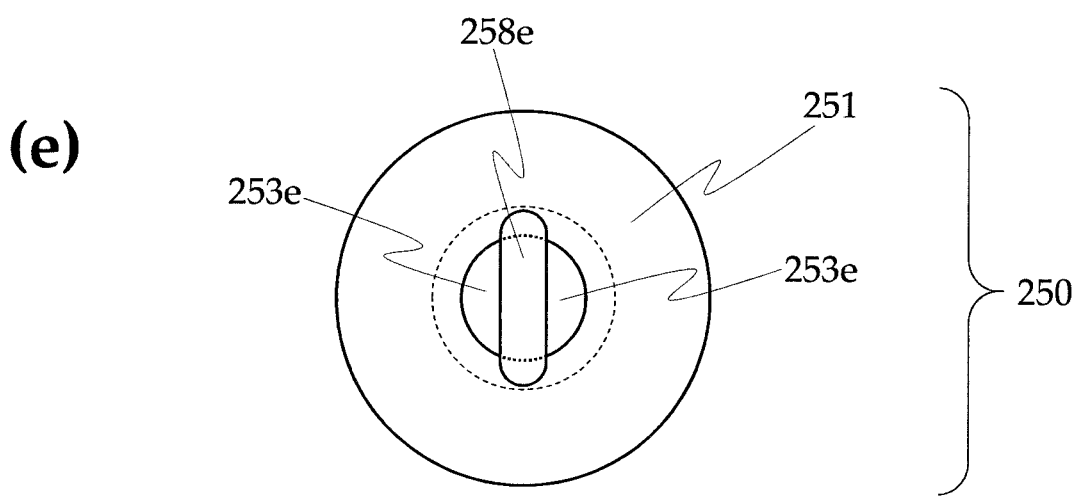
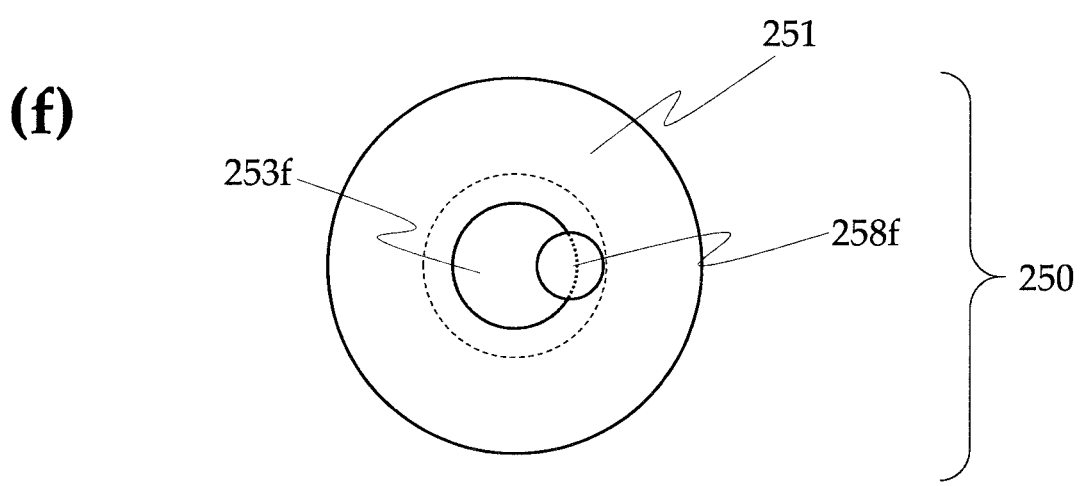

Fig. 6
(a)
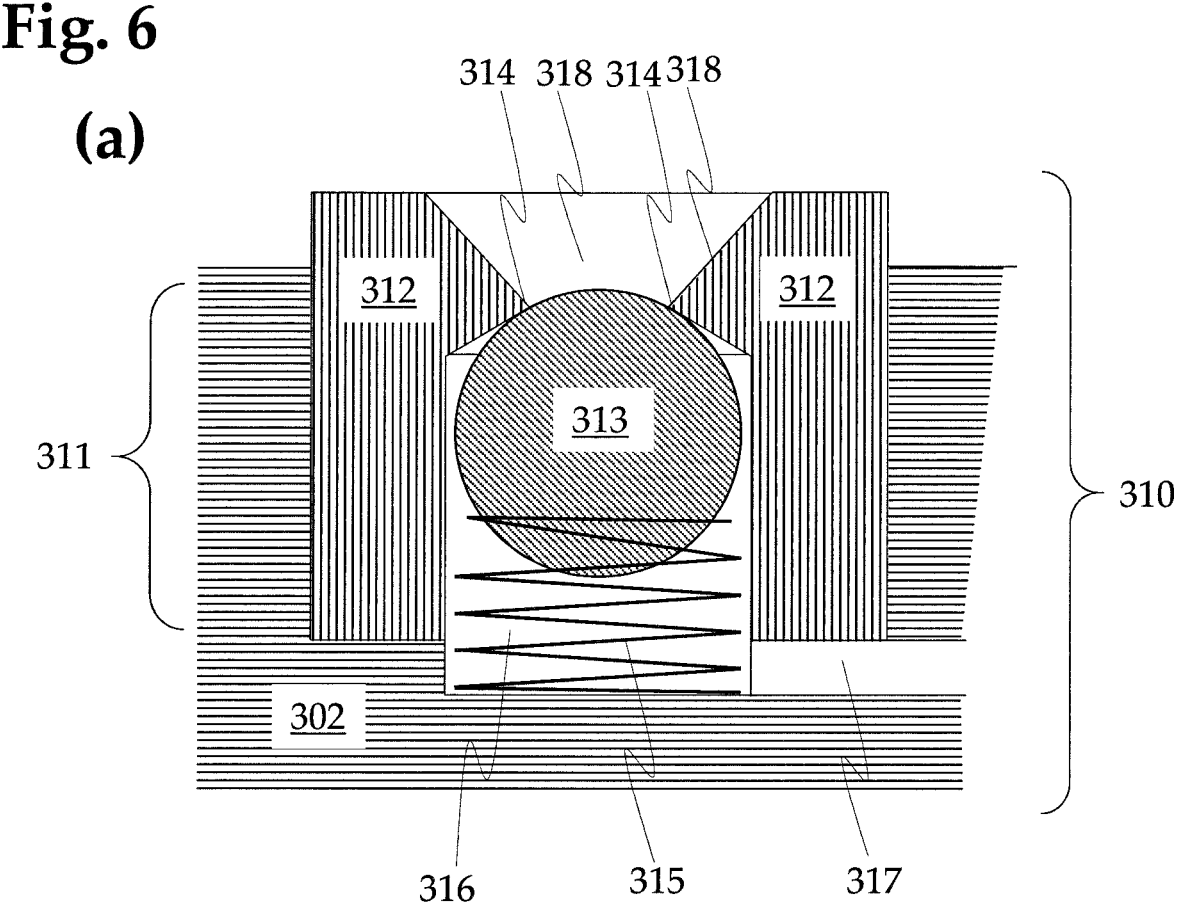
(b)
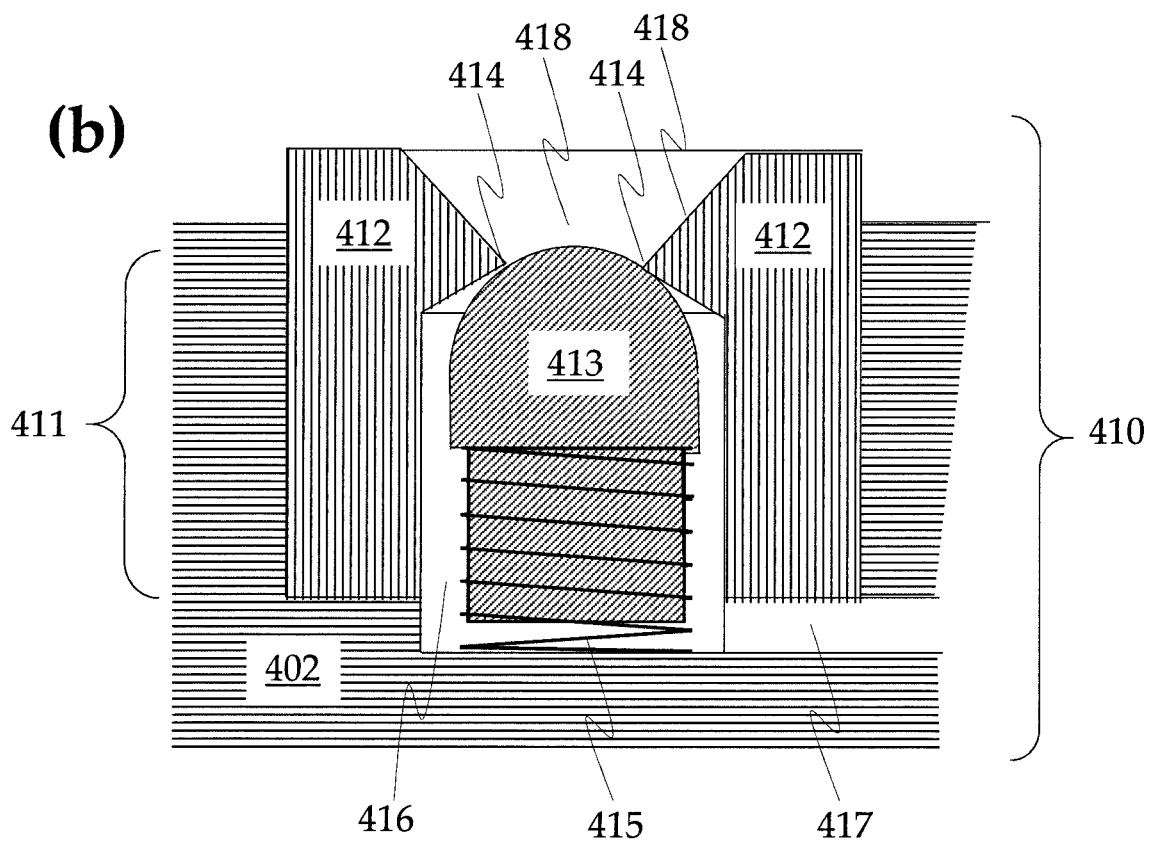

CONNECTOR DEVICE

CROSS REFERENCE TO RELATED APPLICATIONS

This application is a national stage of International Patent Application Number PCT/EP2017/070906, filed Aug. 18, 2017. International Patent Application Number PCT/EP2017/070906, filed Aug. 18, 2017, claims the benefit of European Patent Application Number 16186167.9, filed Aug. 29, 2016.

FIELD OF THE INVENTION

The invention relates to connector devices for fluidly connecting different units of an ambulatory infusion pump system, and connector parts of such connector devices, according to the preamble of the independent claims.

BACKGROUND OF THE INVENTION

Infusion pumps are used for parenterally providing patients with liquid medicaments over longer time periods. Nowadays, infusion pumps with very small dimensions are available that can be carried by the patient on the body. Such small-sized ambulatory infusion pumps are particularly useful for metering small doses of highly effective liquid medicaments, such as insulin for the treatment of diabetes, or analgesics for pain therapy, which are conveyed through a cannula into the tissue of a patient. The treatment of diabetes for example comprises the repeated metering of small doses in the range of nanoliters.

In one approach, an infusion pump, carried somewhere on the body, e.g. attached to a belt, is fluidly connected via flexible tubing to an infusion site interface, also called insertion head, that is attached to the body of the patient. The infusion site interface comprises a cannula unit with a cannula to be inserted into the body tissue, a housing to which the cannula is mounted, and connector means for fluidly connecting the cannula with the flexible tubing connected to the upstream infusion pump. The tubing can be repeatedly connected and disconnected from the infusion site interface. The connector means may for example comprise a septum sealingly closing the fluid system of cannula and housing. The septum can be penetrated by a hollow connector needle, for reversibly establishing a fluid connection. The cannula can be realized as a rigid or semi-rigid cannula with a pointed end that is stiff enough for being inserted into the body tissue on its own, similar to an injection needle. Alternatively, the cannula may be made of a flexible material. Such flexible cannulas are more comfortable during use. Since flexible cannulas cannot be inserted directly into the tissue, an additional piercing device, e.g. in the form of a rigid piercing needle made from metal, is arranged inside the flexible cannula. A pointed end of the piercing device protrudes from the proximal end of the cannula, the cannula that will be open toward the interstitial fluid. After inserting the piercing device and the stabilized cannula into the body tissue, the piercing device is removed from the cannula. The cannula is now flexible, and remains in the body tissue. Generally, a piercing needle is arranged in such a way that it penetrates a septum, which after withdrawal of the piercing needle sealingly closes the distal end of the now open cannula fluid path. Examples of such infusion site interfaces and insertion heads are shown in WO 02/07804 A1, US 2008/0288144 A1, and US 2012/296290 A1, the disclosure of which is hereby included by reference in their entirety In another approach, the infusion pump device is directly fluidly connected with the infusion site interface (so called patch pumps). Examples of such embodiments are shown in WO 2007/056504 A1, the disclosure of which is hereby included by reference in its entirety. The infusion site interface may comprise a base plate adhesively connected to the body surface of the patient. The infusion pump unit is then mounted the base plate, for example with a suitable locking mechanism. The fluid connection between infusion pump and cannula is established by a hollow connector needle of the pump, reversibly penetrating a septum of the cannula unit that sealingly closes the distal end of the cannula fluid path. Advantageously, the pump can be repeatedly connected and disconnected from the infusion site interface. For example may a pump unit be replaced by another pump unit, using the same infusion site interface, or the same pump unit may be used with a further infusion site interface mounted at another location of the patient's body.

FIG. 1 schematically shows a cannula unit of an infusion site interface as it is known from the prior art. The cannula unit comprises a housing body 2, made from a suitable thermoplastic polymer material. In an infusion site interface, the housing body will be suitably mounted on the rest of the interface, e.g. on a base plate (not shown).

The housing body 2 is provided with a passageway along a longitudinal axis of the body, connecting two opposite ends of the body. On one end, a pierceable septum 3 is arranged in a corresponding septum seat 3a, thereby sealingly closing this end of the passageway. On the opposite end, a distal end of an infusion cannula 7 is embedded in the housing body 2. The passageway between septum 3 and cannula 7 defines a conical fluid chamber 4 and a fluid conduit 5. A hollow connector needle 6 of an infusion pump, or of an infusion tubing connected to an infusion pump, penetrates septum 3. A flow path between the infusion pump (not shown) and the proximal end of the infusion cannula (not shown) is established, via needle conduit 6a, fluid chamber 4, fluid conduit 5, and cannula conduit 7a, through which during operation liquid medicament is conveyed, as symbolically indicated by dashed arrows.

Such a cannula unit is particularly useful in combination with flexible cannulas, since for insertion of the cannula into the tissue of a patient, a piercing needle can be arranged in the cannula, with a pointed end protruding from the distal end of the cannula, and a distal end penetrating the septum 3. After insertion, the piercing needle is withdrawn from the cannula. The flow path is then fluidly connected to the tissue of the patient, while the septum sealingly separates the fluid chamber from the environment, thereby keeping the inner volume of the cannula unit sterile. The septum can now be used for establishing a fluid connection with an infusion pump, by penetrating the septum with a hollow connector needle 6 shown in FIG. 1.

In alternative embodiments, separate septums may be used for sealing the flow path after withdrawal of the piercing needle, and for connecting the infusion site interface to the infusion pump. A dedicated connector septum may for example be arranged in a lateral wall of the body in such a way that the connector needle penetrates the connector septum perpendicular to the longitudinal axis defined by the cannula. Similar infusion site interfaces are shown in FIG. 1D of US 2012/0296290 A1. If such a variant is combined with a rigid infusion cannula, without the need for a piercing needle, a septum for the piercing needle may be dispensed with.

In prior art cannula units as discussed above, a fluid chamber 4 with a diameter larger than the fluid conduit 5 and the subsequent cannula conduit 7a is needed, for preventing a pointed end 6b of a connector needle 6 accidentally cutting into the inner volume wall of the body 2, which can produce chips of polymer material that may occlude the cannula passageway, or may be conveyed into the tissue of the patient, which is both not acceptable. Furthermore, a collision of the needle 6 and the inner wall of the body 3 may distort the connector needle, which can cause leakage of the septum 3.

While a conical fluid chamber 4 as shown in FIG. 1 in combination with suitable guiding of the movement of the connector needle can solve the above-mentioned problem, it inevitably comprises a considerable volume that is not accessible, and though which no liquid is conveyed. Several microliters of air may be trapped 8 in such a dead volume. Large volumes in an infusion pump fluid system are detrimental for the precision of repeated metering of doses in the nanoliter range, because gases are very elastic compared to liquids. Larger air volumes may further hinder timely detection of occlusions, since the trapped air can be considerably compressed before system pressure increases above a certain warning threshold. Furthermore, temperature changes also lead to a considerable change of the volume of trapped gas, which may cause unwanted dosing of liquid medicament, or sucking of body fluid back into the cannula, which both may cause metering errors.

Thus, infusion site interfaces applying a septum for establishing a fluid connection to the infusion pump will inevitably limit the achievable precision of metering to a certain limit, although the infusion pump may actually be far more precise.

A further disadvantage of using a pierceable septum and a hollow needle for coupling two fluid systems is the restricted number of coupling/decoupling steps that can be carried out. Each time a hollow coupling needle pierces a septum, the polymer matrix of the elastic septum material is cut. After a while, the elastic material of the septum may be damaged to such an extent that it cannot properly close any longer the bores produced by the needle. The septum starts to leak. In addition, after too may piercing steps, the hollow needle may even cut out particles of the septum material, which may cause occlusions, or which may be conveyed into the tissue of the patient.

There is an ongoing need for improvement in the field of connectors for releasably connecting infusion site interfaces with infusion pumps, or with flexible tubing connected to an infusion pump.

OBJECTIVES OF THE INVENTION

It is an overall objective of this invention to provide advantageous connector devices for connecting components of an ambulatory infusion pump system that overcome one or more of the above-mentioned and other problems. Another object of the invention is to provide advantageous connector parts for such connector devices.

Such connector devices should have a reduced trapped air volume. If possible the overall dead volume should also be reduced. Furthermore, the connector device should be able to reliably establish a connection and release the connection for a large number of cycles without decrease of the functionality, particular without the risk of leakages or other functional failures.

Such connector devices and connector parts should be reliable, and cost efficient in large scale manufacture.

A further object of the invention is to provide ambulatory infusion pump devices and components of ambulatory infusion pump devices that comprise such connector devices and/or connector parts.

These and other objects are substantially achieved through the features of the independent claims. In addition, further advantageous embodiments follow from the dependent claims and the description.

SUMMARY OF THE INVENTION

The present invention may comprise one or more of the features recited in the attached claims, and/or one or more of the following features and combinations thereof.

A first connector part according to the invention for establishing a fluid connection with a second connector part according to the invention, as described further below, comprises a valve with a valve seat, a valve member, and a resilient element. The valve seat comprises a valve chamber, and a circular opening with a circumferential sealing lip. The valve member is provided in the valve chamber, and is able to sealingly close the circular opening of the valve seat when being pushed against the circular opening. The resilient element subjects the valve member to a bias force pushing the valve member against the circular opening of the valve seat. The valve member further comprises a circumferential wall around the circular opening, located on the side of the circular opening opposite to the valve chamber. The circumferential wall forms a concave receptacle for receiving a corresponding connection cone of a second connector part, the concave receptacle having the shape of a truncated cone and facing away from the valve chamber, the circular opening being located in the centre of the concave receptacle.

Advantageously, the valve seat is made of an elastomeric polymer.

In an advantageous embodiment of such a first connector part according the invention, the valve member is a valve ball.

Advantageously, in the first connector part the resilient element is an elastic structure made of an elastomeric polymer, or is a helical spring.

The first connector part according to the invention advantageously further comprises an infusion cannula fluidly connected to the valve chamber. In such an embodiment, it is particularly advantageous when the first connector part further comprises a septum arranged at a distal end of the infusion cannula. Even more advantageously, such a first connector part further comprises a piercing needle for temporarily stiffening the infusion cannula, arranged inside the infusion cannula and penetrating the septum. Advantageously, the valve member and the septum are one single piece.

A second connector part according to the invention for establishing a fluid connection with a first connector part according to the invention, as described further above, comprises a right circular truncated cone for being received in a corresponding concave receptacle of a first connector part; a recess at the tip of the truncated cone for actuating a valve member of a first connector part; and a fluid feed conduit. The fluid feed conduit has one or more outlets opening at least partially toward the shell surface of the cone.

In an advantageous embodiment of a second connector part according to the invention, the surface of the recess has the shape of an inverted cone, or forms a section of a hollow sphere.

Alternatively or in addition, the fluid feed conduit has an outlet located on the recess, and one or more notches extending from the outlet across the recess surface to the shell surface of the cone.

In an even more advantageous embodiment of a second connector part according to the invention, the surface of the recess comprises two or more separated areas.

A connector device according to the invention comprises a first connector part according to the invention, and a second connector part according to the invention.

Advantageously, a connector device according to the invention further comprises means for pressing together with a certain force the first connector part and the second connector part.

Alternatively, or in addition, an advantageous embodiment of a connector device according to the invention further comprises means for aligning and/or orienting the first connector part and the second connector part in relation to each other.

Alternatively, or in addition, an advantageous embodiment of a connector device according to the invention further comprises means for releasably fixating the first connector part and the second connector part in a certain defined position relative to each other.

In an advantageous embodiment of such a connector device according to the invention, with the truncated cone of the concave receptacle of the first connector part having a first cone angle α in regard to a longitudinal axis of the cone, and with the right circular truncated cone of the second connector part having a second cone angle β in regard to a longitudinal axis of the cone, the first cone angle α is larger or equal the second cone angle β, and the difference between first cone angle α and second cone angle β is smaller or equal about 20°, advantageously smaller or equal about 15°, and more advantageously lies between about 5° and about 15°.

An ambulatory infusion pump unit according to the invention comprises a second connector part according to the invention, or a first connector part according to the invention.

An infusion site interface according to the invention comprises a first connector part according to the invention, or a second connector part according to the invention.

An ambulatory infusion pump unit with a second connector part according to the invention can then be coupled with an infusion site interface with a first connector part according to the invention. An ambulatory infusion pump unit with a first connector part according to the invention can be coupled with an infusion site interface with a second connector part according to the invention.

An infusion tubing according to the invention for use with an ambulatory infusion pump comprises a first connector part according to the invention, and/or a second connector part according to the invention.

Said infusion tubing according to the invention can then be coupled with an infusion site interface according to the invention, and/or an ambulatory infusion pump unit according to the invention.

An ambulatory infusion pump system according to the invention comprises a connector device according to the invention.

An adapter according to the invention comprises a hollow connector needle, a fluid transfer conduit fluidly connected to the hollow transfer needle, and a first connector part according to the invention, or a second connector part according to the invention, wherein the fluid transfer conduit is fluidly connected to the fluid system of the first connector part or second connector part.

Another adapter according to the invention comprises a connector septum, a fluid chamber sealingly closed by the connector septum, a fluid transfer conduit fluidly connected to the fluid chamber, and a first connector part according to the invention, or a second connector part according to the invention, wherein the fluid transfer conduit is fluidly connected to the fluid system of the first connector part or second connector part.

The above-mentioned adapters according to the invention allow to connect elements and devices such as ambulatory infusion pump units, infusion site interfaces, and infusion tubing equipped with prior art connector parts such as hollow connector needles, and/or septums to be penetrated by said hollow connector needles to be operationally interconnected with ambulatory infusion pump units, infusion site interfaces, or infusion tubing equipped with first connector parts according to the invention and/or second connector parts according to the invention.

BRIEF DESCRIPTION OF THE DRAWINGS

In order to facilitate a fuller understanding of the present invention, reference is now made to the appended drawings. These references should not be construed as limiting the present invention, but are intended to be exemplary only.

FIG. 1 schematically shows a longitudinal section of a cannula unit according to the prior art as discussed further above.

FIG. 2 schematically shows a longitudinal section of an embodiment of a connector device according to the disclosure, with (a) the female connector part of the connector device, the valve being closed; (b) the male connector part of the connector device approaching the female connector part during the connecting step; (c) the two connector parts in the connected stated, the valve being open; (d) the flow path of liquid medicament conveyed by an infusion pump through the connector device, shown by arrows; and (e) a perspective view of the female connector part.

FIG. 3 schematically shows in a perspective view and partial cross section a patch pump system according to the disclosure, comprising an infusion pump unit, an infusion site interface, and the connector device of FIG. 2 for connecting the fluid system of the infusion pump unit to the cannula of the infusion site interface; (a) in the uncoupled state, and (b) in the coupled state.

FIG. 4 schematically shows the patch pump system of FIG. 3 in a perspective view, with (a) the infusion site interface mounted on the body surface, after insertion of the stiffened infusion cannula into the body tissue; (b) after removal of the piercing needle, the infusion site interface now being operative; (c) the infusion pump unit in a partial bottom view; and (d) the infusion pump unit just before being coupled to the infusion site interface.

FIG. 5 schematically shows different advantageous embodiments of female connector parts of connector devices according to the disclosure, in a bottom view; (a) with an arrangement of notches and fluid feed conduit similar to the embodiment of FIG. 2; and (b) to (f) with alternative arrangements of notches and fluid feed conduit.

FIG. 6 schematically shows a longitudinal section of two further advantageous embodiments of male connector parts of connector devices according to the disclosure.

DETAILED DESCRIPTION OF THE INVENTION

The examples provided hereinafter serve as an improved illustration of the present invention, but are not suited for restricting the invention to the features disclosed herein. Components that are identical, or that are identical at least in terms of their function, are designated below by identical or at least comparable reference numbers, e.g. 2, 102, 302, 402.

An advantageous embodiment of a connector device according to the invention is disclosed in FIGS. 2(a)-(e). The connector device comprises a first, female connector part 110 and a second, male connector part 150. In the unconnected state, the fluid system of the separate female connector part 110 is sealed against the environment. When the two connector parts are aligned and are pressed onto each other with a certain force, they establish a fluid connection between their respective fluid systems, while the fluid system remains sealed against environment.

The first, female connector part 110 of a connector device 170 is shown alone, before the removal of the piercing needle 109, in FIG. 2(a). The first connector part 110 comprises a housing body 102, in the given example protruding from a base plate 101 of an infusion site interface. The housing body 102 is limited by perpendicular walls 119, and has an outer shape (not shown) that is not rotationally symmetric, in order to ensure proper alignment with a second connector part 150, as will be discussed further below.

In the housing body 102, a flexible infusion cannula 107 is mounted, with a first, distal end being fixed to the body. A middle section and a second, proximal end protrude from an underside of the base plate 101 opposite to the first connector part 110. A cannula chamber 104 is defined by the volume between distal end of cannula 107 and septum 103, upstream of the inner conduit of the cannula 107. A piercing needle 109 is arranged inside the cannula 107, with a pointed end (not shown) protruding from the proximal end of the cannula. The piercing needle 109 further penetrates a septum 103 for sealing the fluid system after removal of the piercing needle from the infusion cannula. With the piercing needle 109 inserted in the flexible cannula 107, cannula and needle can be inserted into the tissue of the patient.

The actual connector part 110 comprises a concave connection cone 118 and a valve 111. The connection cone 118 is intended to be pressed against a corresponding connection cone 151 of a second connector part 150, thereby establishing a sealed connection. As long as no connection with a second connector part is established, the connector valve 111 sealingly closes the fluid system of the first connector part against environment. The valve 111 comprises a valve seat 112 with a circumferential sealing lip 114, and a valve member 113 having the shape of a ball. The ball member is mounted on a resilient element 115, which presses with a certain bias force the valve member ball 113 against the circumferential sealing lip 114, thereby sealingly closing the valve. The valve seat 112, the valve member 113 and the resilient element 115 define an inner volume of the valve, the valve chamber 116. A narrow transfer conduit 117 connects the valve chamber 116 with the cannula chamber 104 upstream of the inner conduit of the cannula 107. The shown embodiment has a dead volume that is very small compared to a prior art cannula unit, as for example shown in FIG. 1. No voluminous cannula chamber is needed to prevent damages by connector needles. Furthermore essentially the complete fluid system is in the flow path of the liquid medicament, such that no air bubbles can accumulate and the amount of trapped air is minimal.

Housing body 102 and base plate 101 are made from a suitable rigid polymer material, for example a thermoplastic polymer such as polypropylene. The valve member 112 and the connection cone 118, as well as the septum 103 are realized as one single element, made from a suitable elastomeric polymer material, for example rubber, silicone elastomers, thermoplastic elastomers, and the like. The spherical valve member 113 is made from a rigid, hard material such as for example hard, non-elastic polymers, steel, glass, ceramics etc, and advantageously has a smooth surface. The resilient element 115 is made from a suitable elastomeric polymer material, similar as discussed above for the valve seat 112, connection cone 118, and septum 103. The elastic material should be able to provide the necessary bias force of the valve member 113 against sealing lip 114. All materials that come into contact with liquid medicament or body tissue must be acceptable for that purpose. A skilled person knows which materials are suitable for the intended function of the various elements.

For manufacturing the first connector part 110, the various elements 102, 112/118/103, 115, 107, 109 may be assembled in different order, depending on the specific manufacturing method. In one possible approach, for example, a piercing needle 109 threaded on the cannula 107 is provided, and is partially embedded in the polymer matrix of the housing body 102 and the base plate 101 during the manufacture of housing body and base plate, using suitable injection moulding tooling. A resilient element 115 is mounted on the base plate, or is produced together with the housing body/base plate using two-component injection moulding techniques. Then the valve ball 113 is placed on the resilient element 115. A single component including valve seat, connection cone and septum, is produced e.g. by injection moulding, and is finally inserted in a corresponding seat 125 in the form of a cavity in the housing body 102. During this insertion step, advantageously the distal end of the piercing needle penetrates the septum, arriving at the connector part shown in FIG. 2(a). In a further step, the distal end of the piercing needle may be equipped with a handle for easing removal of the needle.

The second, male connector part 150 of the connector device 170 in the unconnected state can be seen in FIGS. 2(b) and (e), as well as in FIG. 5(a). A connection cone 151 is arranged at the bottom of a cavity 157 with perpendicular walls 155. A spherically shaped recess 153 is located in the centre of the cone 151. The radius of the spherical recess 153 is essentially identical to the radius of the valve member 113, since it has the purpose of keeping the valve member ball aligned when the valve is opened, as will be explained further below. In the centre of the recess, a fluid feed conduit 152 opens toward the outside. The fluid feed conduit 152 is connected to the fluid system downstream of an infusion pump, or to an infusion tubing. Two notches 154 extending radially from the fluid conduit outlet 158 are provided. The depth of the notches 154 is chosen such that they extend into a central zone of the cone surface around the spherical recess 153, but not into an outer zone of the cone surface that will come into contact with the surface counter cone 118 of a first connector part for establishing. In FIG. 5(a), these two zones are schematically made visible by a dashed circle defining the inner zone and the outer zone of the cone surface.

The second connector part 150 is preferably made of a rigid, hard polymer material, such as for example a suitable thermoplastic polymer. Other hard materials such as metal, glass or ceramic material would also be possible, although more expensive and more difficult to manufacture.

A connector device advantageously comprises primary guiding structures that ensure proper orientation and alignment of the two connector parts. In the given embodiment, such primary guiding structures are provided in the form of interacting guiding elements 119, 155. The guiding element 119 of the first connector part 110 is realized as an outer wall 119 of the housing body 102, extending perpendicularly from the base plate 101. The guiding element 155 of the second connector part 150 is realized as an inner wall 155 of a cavity 157, extending perpendicularly from the bottom of the cavity, at the bottom of which the connector components are arranged (cf. FIG. 2(e)). The two guiding walls 119, 155 are shaped in such a way that proper orientation of the two connector parts 110, 150 is given during the connecting process. In other words, the two connector parts can only be assembled in one, correct orientation. In the given example, a rotationally non-symmetric, egg-shaped form of the walls 155 of the cavity 157 and the outer walls 119 of the housing body 102 allows a coupling only with the two connector parts 110, 150 properly aligned to a coupling axis 161, in one specific rotational arrangement of the two connector parts 110, 150.

The situation during the connection process is shown in FIG. 2(b), just before the connection of the two connector parts 110, 150 of the disclosed connector device 170 is established. The infusion cannula has been inserted into the body tissue 191 of a patient, and the base plate 101 of the infusion site interface has been attached to the body surface. The piercing needle has been removed. The two connector parts 110, 150 are properly aligned along axis 171 and correctly oriented to each other. The outer guiding wall 119 has been inserted into the corresponding cavity 157 with inner guiding walls 155. During the connection movement of the two connector parts 110, 150, symbolized by an arrow, the guiding walls 119, 155 glide along each other along coupling axis 171.

FIG. 2(c) shows the connector device 170 with established connection between the two connector parts 110, 150. The connection cone 151 is pressed with a certain force into the concave connection cone 118. Since the concave connection cone 118 is made of an elastomeric polymer material, while the connection cone 155 is made of a hard, inelastic material, the elastic, resilient cone 118 will be deformed in the zone the two cones come into contact, thereby establishing a reliable fluidly sealed connection between the first and the second connector part.

Advantageously, the inclination angle of the connection cone 155 in regard to its longitudinal axis is chosen slightly larger than the corresponding inclination angle of its counter cone 118, which results in a circumferential contact zone between the two cones extending from the centre axis 171 radially outwards, with the highest contact pressure close to the centre axis. Such an embodiment prevents air being present between the surfaces of the two contacting cones of being pressed into the fluid system. The air is safely squeezed outwards toward atmosphere.

During the coupling process, just before the two connection cones 118, 151 start to touch, the spherical recess 153 will touch down on the ball valve member 113. During the remaining forward movement of the cone 151, during which the cones start to abut to each other and cone 118 is slightly compressed in the contact zone, the valve member 113 will be pushed downwards toward the base plate, against the bias force of resilient element 115 (shown as dashed arrow). As a result, the valve member ball 113 no longer abuts the sealing lip 114, and the connector valve 111 is open. Thus, in the disclosed embodiment of a connector device, the connection cone 151 of the second connector device 150 acts as an actuator for the valve member 113 of valve 111 of the first connector device 110. Since both cone 151/spherical recess 153 and valve member 113 consist of a hard, inelastic material, while cone 118 is resilient, the movement of the valve member 113 by cone 151 is precise.

For being properly connected and operative, the two connector parts of a connector device as discussed above, particularly their respective connection cones 151 and 118, need to be brought into and hold in a certain, defined position in regard to each other. In this position, a sealingly tight connection between the two cones is achieved, and the valve is kept open by holding the valve ball in its open position against the closing bias force of the resilient element. The correct positioning of the two connector parts can be achieved by suitable guiding and locking means that correctly align the two connector parts and keep them in a certain distance to each other. Such guiding and locking means may be provided directly in the connecting device, or may be provided in a higher-level system, for example by the means for locking a patch infusion pump on an infusion site interface. Corresponding technologies are well known to a skilled person, e.g. releasable clamp mechanisms, bayonet couplings, etc.

Liquid medicament can now be conveyed downstream from the infusion pump into the infusion cannula toward the body tissue 191 of the patient, as schematically shown as arrows in FIG. 2(d). Liquid flows downstream through fluid feed conduit 152, toward the outlet 158 of the conduit. Since the outlet 158 is blocked by valve ball 113, the fluid flows through two conduits between spherical recess 153 and valve member 113, provided by the two notches 154, into the now accessible valve chamber 115. In the valve chamber 115, the liquid flows between valve seat 112 and valve member 113 downward, around the resilient element 115, through the transfer conduit 117 into the cannula chamber 104. From the cannula chamber, the liquid finally flows through cannula conduit 107a towards the proximal end of the cannula, into the tissue 191 of the patient.

For releasing the connection between the two connector parts 110, 150, the connecting process is reversed. When the second connector part 150 is moved upwards, away from the first connector part, the valve member ball 113 will also move upwards, driven by the biasing force of the resilient element 115, until it reaches the sealing lip 114 of the valve member 112. The valve 111 is now sealingly closed again, protecting the fluid system against environment. During the closing movement of the valve member, the compressed elastic cone 118 expands, but keeping its cone surface abut the cone surface of cone 151.

A further upward movement of second part 150 separates the two cones. The two connector parts are decoupled.

The shown embodiment of a connector device can be used as an advantageous alternative to known septum/needle connector devices, and may be applied for infusion site interfaces intended for being connected to infusion tubing connector, as well as for being directly coupled to an infusion patch pump unit. FIGS. 3 and 4 shows such a patch pump system, using the connector device of FIG. 2.

The patch pump system comprises an infusion pump unit 160 and a corresponding infusion site interface 161. The infusion site interface 161 comprises a base plate 101, which is attachable with its flat underside to a body surface of a patient, e.g. in the region of an upper arm, a thigh, or the abdomen. Suitable attaching methods are known from the prior art, for example using adhesive layers provided on the underside of the base plate. The infusion site interface further comprises a first connector part 110, like the one disclosed in FIG. 2, a cannula 107, and a piercing needle 109 (not shown in FIG. 3). The infusion pump unit 160 comprises a second connector part 150 located in cavity 157, similar to the one disclosed in FIG. 2. Since portable infusion pumps that can be integrated in a patch pump 160 are known from the prior art, no details are shown regarding the pump system upstream of fluid feed conduit 152. The infusion pump unit 160 can be releasably mounted to the upper side of the infusion site interface 161, with suitable locking means. Locking means that can be used for such a purpose, e.g. releasable catch lock mechanisms or the like, are known to the skilled person and are not shown in detail. The locking means, in addition to securely mounting the infusion pump unit to the base plate of the infusion site interface, have two additional purposes. On one hand the locking means act as secondary guiding elements for the connector device, which ensure a correct orientation of the two connector parts before the guiding walls 119, 155 as the primary guiding elements abut each other and ensure a precise alignment during the connection step. On the other hand, the locking means will hold the infusion pump unit and the infusion site interface tightly fixed to each other, thereby constantly holding the pressing force on the two connector parts.

For setting the patch pump system in operation, in a first step shown in FIG. 4(*a*), the infusion site interface 161 is placed on the body surface of the patient. In the shown embodiment, the temporarily stiffened infusion cannula 107 is inserted into the tissue during manually placing the base plate 101 on the body.

So called inserter devices are known that allow in a first step attaching a base plate on the body, and in a second step automatically inserting a stiffened cannula into the body tissue, fixedly attaching a cannula hub to the base plate, and subsequently withdrawing the piercing needle. Such technologies can also be applied for connector devices as disclosed. In such a case, a hub comprising the housing body with the cannula and the first connector device would be fixedly attached to the base plate after insertion of the temporarily stiffened cannula.

In the shown embodiment, however, the piercing needle 109 is removed manually, and one arrives at the now operative infusion site interface 161 in FIG. 4(*b*). The infusion pump device 160 is prepared for being attached to the infusion site interface 161 (FIG. 4(*c*)), and is mounted to the base plate (FIG. 4(*d*)).

As has been shown, in order to establish a fluid connection between the fluid feed conduit of a second connector part and the fluid system of a first connector part, the liquid has to pass the abutting spherical recess and valve member ball. In the embodiment of a connector device as discussed above, this has been achieved by two notches extending from the feed conduit outlet in the centre of the spherical recess to the inner zone of the cone that is not in contact with the cone of the first connector part. Such an arrangement is also shown in FIG. 5(*a*).

FIGS. 5(*b*) to (*f*) show further, alternative arrangements of the various elements on the connecting cone of a second connector. Dotted circles mark the borderline between the outer zone of the cone 251, which contacts the counter cone of the other connector part, and the inner zone, which faces toward the valve chamber once the valve is opened. FIG. 5(*b*) shows an alternative embodiment where only one notch 254 extends from the outlet 258, thus representing a minimum variant. FIG. 5(*c*) shows a further embodiment, with three notches 254, providing an increased flow cross section. Similarly, the amount of notches can be further increased, and/or the geometry of the notches can be changed to more complex forms. Essentially, the area of the spherical recess may be reduced to a very minimum as long as it allows a precise and reliable actuation of the valve member. An embodiment with strongly reduced spherical recess area is depicted in FIG. 5(*d*). The notches have been extended to a circular plane 254*d* perpendicular to the coupling axis, into which the outlet 258 opens. The spherical recess has been reduced to four segment shaped protrusions extending from the plane 254*d*, having a front face 253*d* that represents a section of the same spherical shape. In such an embodiment, a valve ball of a first connector part will only be in contact with the front faces 253*d* of the three protrusions, while the liquid can flow through the free volume between the circular plane 254*d* and the valve ball surface.

A further embodiment of a connector cone, which does not make use of notches, is shown in FIG. 5(*e*). The fluid feed conduit and its outlet 258*e* have an oblong cross-section, which extends from the centre of the spherical recess 253 into the inner zone of the cone 251. As a result, the two outer areas of the outlet 258*e* that are not within the circular area of the spherical recess 253 open directly toward the valve chamber, once the valve is open. A similar approach is applied in the embodiment disclosed in FIG. 5(*f*). The fluid feed channel and its outlet 258*f* are not aligned to the coupling axis, but are located off-centre.

At least a part of the outlet cross-section lies in the inner zone of the cone surface of cone 251. This area of the outlet 258*f* directly opens toward the valve chamber, once the valve is open.

Further embodiments of a first connector part of a connector device are shown in FIG. 6. The functional principle of the first connector parts 310, 410 is essentially the same as for the first connector part shown in FIG. 2.

The embodiment 310 as shown in FIG. 6(*a*) differs from the previously discussed first connector part in that the bias force pressing the valve member 313 against sealing lip 318 of valve seat 312 is generated with a helical spring 315. Furthermore, valve member 312 with connection cone 318 does not include a septum for the piercing needle. The septum (not shown) is either realized as a separate element, or is dispensed with, for example when rigid cannulas are used.

In the embodiment of a first connector part 410 as shown in FIG. 6(*b*), the ball shaped valve member has been replaced by an essentially cylindrical valve member 413. One end of this cylinder is arranged inside the helical spring 415, thereby ensuring the alignment of valve member 413 and spring 415, and reducing the volume of the valve chamber. Another end of the valve member, facing toward the sealing lips 414 of the valve member 412, is realized as a half sphere. The helical spring 415 is supported on a circumferential edge of the cylinder.

In the embodiments discussed so far, the fluid feed conduit of the second connector part has opened in an outlet that is the connected state is at least partially blocked by the valve member of the first connector part. Such components can be efficiently produced, e.g. with injection moulding techniques. However, principally it would also be possible to dispense with the outlet, and to provide a fluid connection between a fluid feed conduit in the form of a blind hole and the inner zone of the cone surface with one or more dedicated conduits branching off from the fluid feed conduits.

The present invention is not to be limited in scope by the specific embodiments described herein. Indeed, various modifications of the present invention, in addition to those described herein, will be apparent to those skilled in the art from the foregoing description and accompanying drawings. Thus, such modifications are intended to fall within the scope of the appended claims. Additionally, various references are cited throughout the specification, the disclosures of which are each incorporated herein by reference in their entirety.

LIST OF REFERENCE NUMERALS 2 housing body
3 connector septum
3a septum seat
4 fluid chamber
5 fluid conduit
6 connector needle
6a needle conduit
6b pointed end of needle
7 infusion cannula
7a cannula conduit
8 trapped air
10 first connector part
50 second connector part
70 connector device
100 insertion head
101 base plate
102 housing body
103 septum
104 cannula chamber
107 infusion cannula
109 piercing needle
110 first connector part, female connector part
111 connector valve
112 valve seat
113 valve member, valve ball
114 sealing lip
115 resilient element
116 valve chamber
117 fluid transfer conduit
118 concave connection cone
119 guiding element, guiding wall
125 cavity for valve seat and septum
150 second connector part, male connector part
151 connection cone
152 fluid feed conduit
153 spherical recess
154 notch
155 guiding element, guiding wall
157 cavity
158 outlet of fluid feed conduit
160 infusion pump unit
161 infusion site interface
170 connector device
171 coupling axis
190 body surface
191 body tissue
250 second connector part
251 connection cone
253 spherical recess
253d spherical front face of a protrusion
253e spherical recess
253f spherical recess
254 notch
254d circular plane
258 outlet of fluid feed conduit
258e outlet of fluid feed conduit
258f outlet of fluid feed conduit
302 housing body
310 first connector part
311 valve
312 valve seat
313 valve member, ball
314 sealing lip
315 spring element
316 valve chamber
317 fluid transfer conduit
318 concave connection cone
402 housing body
410 first connector part
411 valve
412 valve seat
413 valve member
414 sealing lip
415 spring element
416 valve chamber
417 fluid transfer conduit
418 concave connection cone

The invention claimed is:
1. A connector device, comprising:
a first connector part;
a second connector part;
the first connector part for establishing a fluid connection with the second connector part, the first connector part comprising
a valve with a valve seat, the valve seat comprising a valve chamber and a circular opening with a circumferential sealing lip;
a valve member, the valve member being provided in the valve chamber, and being able to sealingly close the circular opening of the valve seat when being pushed against the circular opening;
a resilient element that subjects the valve member to a bias force pushing the valve member against the circular opening of the valve seat;
wherein the valve member seals with the circumferential sealing lip when the resilient element pushes the valve member against the circular opening of the valve seat;
wherein the valve member further comprises a circumferential wall around the circular opening, located on a side of the circular opening opposite to the valve chamber;
wherein the circumferential wall forms a concave receptacle for receiving a corresponding connection cone of the second connector part, the concave receptacle having a shape of a truncated cone and facing away from the valve chamber, the circular opening being located in a centre of the concave receptacle;
wherein the concave receptacle has a first cone angle $\alpha$ in regard to a longitudinal axis of the truncated cone;
wherein the first cone angle $\alpha$ is larger than a second cone angle $\beta$ of the second connector part;
wherein a difference between the first cone angle $\alpha$ and the second cone angle $\beta$ lies between 5° and 20°;
wherein the difference between the first cone angle $\alpha$ and the second cone angle $\beta$ creates a circumferential contact zone between the concave receptacle and the corresponding connection cone;
wherein the concave receptacle of the valve seat is made of resilient material; and
wherein the corresponding connection cone and the valve member are made of hard, inelastic material to facilitate precise movement of the valve member.

2. The connector device according to claim 1, wherein the valve seat is made of an elastomeric polymer.

3. The connector device according to claim 1, wherein the valve member is a valve ball.

4. The connector device according to claim 1, wherein the resilient element is an elastic structure made of an elastomeric polymer, or is a helical spring.

5. The connector device according to claim 1, further comprising an infusion cannula fluidly connected to the valve chamber.

6. The connector device according to claim 5, further comprising a septum arranged at a distal end of the infusion cannula.

7. The connector device according to claim 6, further comprising a piercing needle for temporarily stiffening the infusion cannula, arranged inside the infusion cannula and penetrating the septum.

8. The connector device according to claim 6, wherein the valve member and the septum are one single piece.

9. An ambulatory infusion pump unit, comprising the connector device according to claim 1.

10. An infusion site interface, comprising the connector device according to claim 1.

11. An adapter comprising a hollow connector needle, a fluid transfer conduit fluidly connected to the hollow connector needle, and the connector device according to claim 1, wherein the fluid transfer conduit is fluidly connected to a fluid system of the connector device.

12. An adapter comprising a connector septum, a fluid chamber sealingly closed by the connector septum, a fluid transfer conduit fluidly connected to the fluid chamber, and the connector device according to claim 1, wherein the fluid transfer conduit is fluidly connected to a fluid system of the connector device.

13. A connector device, comprising:
a first connector part;
a second connector part;
the second connector part for establishing a fluid connection with the first connector part, the second connector part comprising
a right circular truncated cone for being received in a corresponding concave receptacle of the first connector part;
a recess at a tip of the right circular truncated cone for actuating a valve member of the first connector part, wherein the circular truncated cone has a shell surface;
a fluid feed conduit;
wherein the tip of the right circular truncated cone defines one or more notches that extend in an outer radial direction;
wherein the first connector part has the corresponding concave receptacle with a first cone angle α in regard to a longitudinal axis of the right circular truncated cone;
wherein the first cone angle α is larger than a second cone angle β of the second connector part;
wherein a difference between the first cone angle α and the second cone angle β lies between 5° and 20°;
wherein the valve member is made is made of a hard, rigid material; and
wherein the second connector part is made of a hard, rigid material.

14. The connector device according to claim 13, wherein a surface of the recess has a shape of an inverted cone or forms a section of a hollow sphere.

15. The connector device according to claim 13, wherein the fluid feed conduit has an outlet located on the recess, and the one or more notches extending from the outlet across a surface of the recess to the shell surface of the right circular truncated cone.

16. The connector device according to claim 13, wherein a surface of the recess comprises two or more separated areas.

17. The connector device according to claim 13, comprising:
the first connector part for establishing the fluid connection with the second connector part, wherein the first connector part is part of an infusion site interface, comprising
an infusion cannula;
a valve for establishing the fluid connection, wherein the valve comprises a valve seat, the valve seat comprising a valve chamber, and a circular opening with a circumferential sealing lip;
the valve member, the valve member being provided in the valve chamber, and being able to sealingly close the circular opening of the valve seat when being pushed against the circular opening; and
a resilient element that subjects the valve member to a bias force pushing the valve member against the circular opening of the valve seat;
wherein the valve seat further comprises a circumferential wall around the circular opening, located on a side of the circular opening opposite to the valve chamber; and
wherein the circumferential wall forms the corresponding concave receptacle for receiving the right circular truncated cone of the second connector part, the corresponding concave receptacle having a shape of a truncated cone and facing away from the valve chamber, the circular opening being located in center of the corresponding concave receptacle.

18. An ambulatory infusion pump system, comprising the connector device according to claim 17.

19. The connector device according to claim 17, further comprising a means for pressing together with a certain force the first connector part and the second connector part.

20. The connector device according to claim 17, further comprising a means for aligning and/or orienting the first connector part and the second connector part in relation to each other; and/or a means for releasably fixating the first connector part and the second connector part in a certain defined position relative to each other.

21. An ambulatory infusion pump unit, comprising the connector device according to claim 13.

22. An infusion site interface, comprising the connector device according to claim 13.

23. An infusion tubing for use with an ambulatory infusion pump, comprising the connector device according to claim 13, the first connector part for establishing the fluid connection with the second connector part, wherein the first connector part is part of an infusion site interface, comprising
an infusion cannula;
a valve for establishing the fluid connection, wherein the valve comprises a valve seat, the valve seat comprising a valve chamber and a circular opening with a circumferential sealing lip;

the valve member, the valve member being provided in the valve chamber, and being able to sealingly close the circular opening of the valve seat when being pushed against the circular opening; and a resilient element that subjects the valve member to a bias force pushing the valve member against the circular opening of the valve seat;

wherein the valve seat further comprises a circumferential wall around the circular opening, located on a side of the circular opening opposite to the valve chamber; and wherein the circumferential wall forms the corresponding concave receptacle for receiving the right circular truncated cone of the second connector part, the corresponding concave receptacle having a shape of a truncated cone and facing away from the valve chamber, the circular opening being located in center of the corresponding concave receptacle.

24. An adapter comprising a hollow connector needle, a fluid transfer conduit fluidly connected to the hollow connector needle, and the connector device according to claim 13, wherein the fluid transfer conduit is fluidly connected to a fluid system of the second connector part.

25. An adapter comprising a connector septum, a fluid chamber sealingly closed by the connector septum, a fluid transfer conduit fluidly connected to the fluid chamber, and the connector device according to claim 13, wherein the fluid transfer conduit is fluidly connected to a fluid system of the connector device.

26. A connector device, comprising:
a first connector part;
a second connector part;
the first connector part for establishing a fluid connection with the second connector part, wherein the first connector part is part of an infusion site interface, comprising an infusion cannula;
a valve for establishing the fluid connection, wherein the valve comprises a valve seat, the valve seat comprising a valve chambers and a circular opening with a circumferential sealing lip;
a valve member, the valve member being provided in the valve chamber, and being able to sealingly close the circular opening of the valve seat when being pushed against the circular opening; and
a resilient element that subjects the valve member to a bias force pushing the valve member against the circular opening of the valve seat;
wherein the valve seat further comprises a circumferential wall around the circular opening, located on a side of the circular opening opposite to the valve chamber;
wherein the circumferential wall forms a concave receptacle for receiving a right circular truncated cone of the second connector part, the concave receptacle having a shape of a truncated cone and facing away from the valve chamber, the circular opening being located in a center of the concave receptacle;

the second connector part including
the right circular truncated cone for being received in the concave receptacle of the first connector part, wherein the right circular truncated cone of the second connector part has an outer zone that contacts the concave receptacle of the first connector part and an inner zone that faces towards the valve chamber,
a recess at a tip of the right circular truncated cone for actuating the valve member of the first connector part, wherein the right circular truncated cone has a shell surface, and
a fluid feed conduit;
wherein the fluid feed conduit has one or more notches at least partially toward the shell surface of the right circular truncated cone;
wherein the outer zone contacts the concave receptacle to accurately set a depth of the inner zone to unseat the valve;
wherein the inner zone is received in the circular opening of the valve seat;
wherein the outer zone is located outside of the circular opening of the valve seat;
wherein the valve member unseals from the circumferential sealing lip when the inner zone of the second connector part pushes against the valve member to unseat the valve;
wherein the first connector part has the concave receptacle with a first cone angle $\alpha$ in regard to a longitudinal axis of the truncated cone of the concave receptacle;
wherein the first cone angle $\alpha$ is larger than a second cone angle $\beta$ of the second connector part;
wherein a difference between the first cone angle $\alpha$ and the second cone angle $\beta$ creates a circumferential contact zone between the concave receptacle and the right circular truncated cone;
wherein the circumferential contact zone is located at the outer zone of the second connector part;
a septum arranged at a distal end of the infusion cannula;
wherein the right circular truncated cone presses against the truncated cone of the concave receptacle to inhibit further movement for facilitating precise opening of the valve member;
wherein the valve seat, the truncated cone and the septum are realized as a one single element made of an elastomeric polymer material; and
wherein the right circular truncated cone and the valve member are made of hard, inelastic material to facilitate precise movement of the valve member.

27. The connector device according to claim 26, wherein the difference between the first cone angle $\alpha$ and the second cone angle $\beta$ lies between about 5° and about 15°.

* * * * *